(12) United States Patent
Kuehn

(10) Patent No.: US 9,023,098 B2
(45) Date of Patent: May 5, 2015

(54) DUAL VALVE PROSTHESIS FOR TRANSCATHETER VALVE IMPLANTATION

(75) Inventor: Stephen Kuehn, Woodbury, MN (US)

(73) Assignee: Medtronic, Inc., Minneapolis, MN (US)

(*) Notice: Subject to any disclaimer, the term of this patent is extended or adjusted under 35 U.S.C. 154(b) by 143 days.

(21) Appl. No.: 13/432,950

(22) Filed: Mar. 28, 2012

(65) Prior Publication Data

US 2013/0261739 A1    Oct. 3, 2013

(51) Int. Cl.
*A61F 2/24* (2006.01)

(52) U.S. Cl.
CPC ............ *A61F 2/2418* (2013.01); *A61F 2/2412* (2013.01); *A61F 2/2433* (2013.01); *A61F 2220/0025* (2013.01); *A61F 2250/0039* (2013.01); *A61F 2250/006* (2013.01); *A61F 2220/0075* (2013.01); *A61F 2230/001* (2013.01); *A61F 2230/0054* (2013.01)

(58) Field of Classification Search
CPC ....... A61F 2/2418; A61F 2/2412; A61F 2/24; A61F 2/2433; A61F 2250/006; A61F 2250/0039; A61F 2220/0025
USPC ...................................... 623/1.11, 2.18, 2.11
See application file for complete search history.

(56) References Cited

U.S. PATENT DOCUMENTS

| 5,957,949 | A | 9/1999 | Leonhardt et al. |
|---|---|---|---|
| 2008/0183273 | A1* | 7/2008 | Mesana et al. ............... 623/1.11 |
| 2009/0248143 | A1* | 10/2009 | Laham .......................... 623/1.26 |
| 2009/0259292 | A1 | 10/2009 | Bonhoeffer |
| 2009/0319038 | A1 | 12/2009 | Gurskis et al. |

FOREIGN PATENT DOCUMENTS

| WO | WO2008/051554 | 5/2008 |
|---|---|---|
| WO | WO2008/091515 | 7/2008 |

* cited by examiner

*Primary Examiner* — Tuan V Nguyen
*Assistant Examiner* — Tin Nguyen

(57) ABSTRACT

A dual valve prosthesis having a self-expanding anchoring frame with first and second prosthetic valve assemblies attached to the anchoring frame is disclosed. Each of the first and second prosthetic valve assemblies includes a balloon-expandable stent structure with a prosthetic valve secured therein. In a disclosed method, the first and second prosthetic valve assemblies include prosthetic mitral and aortic valves, respectively, and the dual heart valve prosthesis is configured to replace both the native mitral and aortic valves of the heart in a single transcatheter heart valve implantation procedure.

20 Claims, 7 Drawing Sheets

DUAL VALVE PROSTHESIS FOR TRANSCATHETER VALVE IMPLANTATION

FIELD OF THE INVENTION

The invention relates generally to a prosthetic valve for replacing a native valve or previously implanted prosthetic valve in a non-surgical interventional procedure. More particularly, the invention relates to a dual valve prosthesis having a prosthetic aortic valve combined with a prosthetic mitral valve for concurrently replacing the corresponding native valve(s) or previously implanted prosthetic valve(s) in a non-surgical interventional procedure.

BACKGROUND OF THE INVENTION

A wide range of medical treatments are known that utilize "endoluminal prostheses." As used herein, endoluminal prostheses are intended to mean medical devices that are adapted for temporary or permanent implantation within a body lumen, including both naturally occurring and artificially made lumens. Examples of lumens in which endoluminal prostheses may be implanted include, without limitation: arteries, veins, gastrointestinal tract, biliary tract, urethra, trachea, hepatic and cerebral shunts, and fallopian tubes.

Stent prostheses are known for implantation within a body lumen for providing artificial radial support to the wall tissue that defines the body lumen. To provide radial support to a blood vessel, such as one that has been widened by a percutaneous transluminal coronary angioplasty, commonly referred to as "angioplasty," "PTA" or "PTCA", a stent may be implanted in conjunction with the procedure. Under this procedure, the stent may be collapsed to an insertion diameter and inserted into the vasculature at a site remote from the diseased vessel. The stent may then be delivered to the desired treatment site within the affected vessel and deployed, by self-expansion or radial expansion, to its desired diameter for treatment.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets disposed within the interior of the stent structure. The prosthetic valve can be reduced in diameter, by being contained within a sheath component of a delivery catheter or by crimping onto a balloon of a dilatation catheter, and advanced through the venous or arterial vasculature. Once the prosthetic valve is positioned at the treatment site, for instance within an incompetent native or previously implanted prosthetic valve, the stent structure may be expanded to hold the prosthetic valve firmly in place. One embodiment of a prosthetic valve having a stent structure is disclosed in U.S. Pat. No. 5,957,949 to Leonhardt et al. entitled "Percutaneous Placement Valve Stent," which is incorporated by reference herein in its entirety.

Valvular heart disease is any disease process involving one or more of the valves of the heart, i.e., the aortic and mitral valves on the left and the pulmonary and tricuspid valves on the right. Severe valve damage may be treated with a valve replacement, with aortic valves and severely damaged mitral valves being the most often replaced heart valves. Some patients present with more than one heart valve being damaged so that the patient may need a dual valve replacement requiring more than one heart valve to be repaired or replaced. Whereas the use of minimally invasive techniques may be preferred, such an approach may be difficult in a dual valve replacement as placement of the prosthetic mitral valve prior to or subsequent of placement of the prosthetic aortic valve may be extremely difficult due to the relative locations of the two native valves and/or the lack of space in the left ventricle, and/or the concern of having to cross the first deployed prosthetic valve with the second delivery system and prosthetic valve under certain circumstances. Moreover, when a prosthetic valve is percutaneously delivered to replace a stenotic or insufficient aortic or mitral valve, a fundamental concern is that the prosthesis be deployed as precisely as possible so as to assure proper functioning, to avoid paravalvular leakage and to minimize any negative impact on the adjacent heart valve, each of which becomes more difficult to achieve with a dual valve replacement performed using multiple prosthetic valves and delivery devices. Further, sufficient prosthetic mitral valve fixation against high systolic pressures is also particularly important as migration or movement of the mitral prosthetic device can potentially block the left ventricular outflow tract or inhibit native or replacement aortic valve function. As such patients who must have a dual valve replacement most often undergo open heart surgical replacement procedures to implant the prosthetic aortic and mitral valves or one of the valves goes untreated. Accordingly a need exists in the art for apparatus and methods that allow a clinician to perform a dual heart valve replacement in a minimally invasive manner.

BRIEF SUMMARY OF THE INVENTION

Embodiments hereof are directed to a dual valve prosthesis having a self-expanding anchoring frame with first and second prosthetic valve assemblies attached to the anchoring frame, wherein each of the first and second prosthetic valve assemblies includes a balloon-expandable stent structure with a prosthetic valve secured therein. In a method in accordance herewith, the first and second prosthetic valve assemblies are prosthetic mitral and aortic valves, respectively, and the dual heart valve prosthesis is configured to replace both the native mitral and aortic valves of the heart in a single transcatheter heart valve implantation procedure.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

The following detailed description is merely exemplary in nature and is not intended to limit the invention or the application and uses of the invention. Although the description of embodiments hereof is in the context of concurrent aortic and mitral heart valve replacement, the invention may be adapted to be used for other concurrent valve replacement where it is deemed useful. Furthermore, there is no intention to be bound by any expressed or implied theory presented in the preceding technical field, background, brief summary or the following detailed description.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. Further the term "self-expanding" is used in the following description with reference to an anchoring frame of the valve prosthesis and is intended to convey that the anchoring frame is shaped or formed from a material that has a mechanical memory to return to an expanded deployed configuration from a compressed or constricted delivery configuration. Non-exhaustive exemplary materials that may be rendered self-expanding include stainless steel, a pseudo-elastic metal such as a nickel titanium alloy or nitinol, various polymers, and a so-called super alloy, which may have a base metal of nickel, cobalt, chromium, or other metal. Mechanical memory may be imparted to a wire or tubular structure used to form the anchoring frame by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

Figure 1:
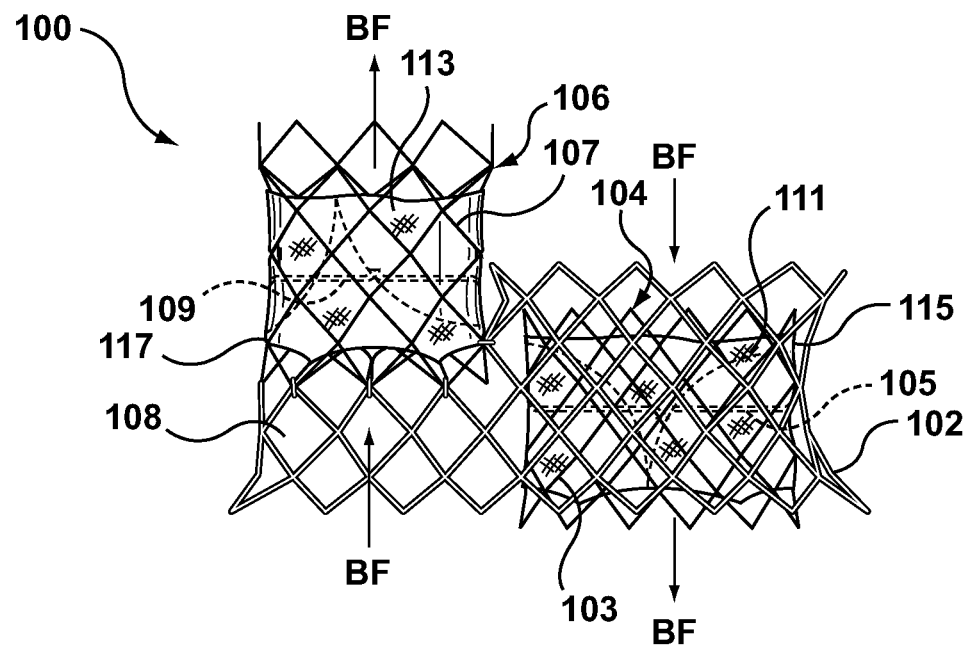
FIG. 1 is a side view of a dual valve prosthesis in an expanded configuration in accordance with an embodiment hereof.
Figure 2:
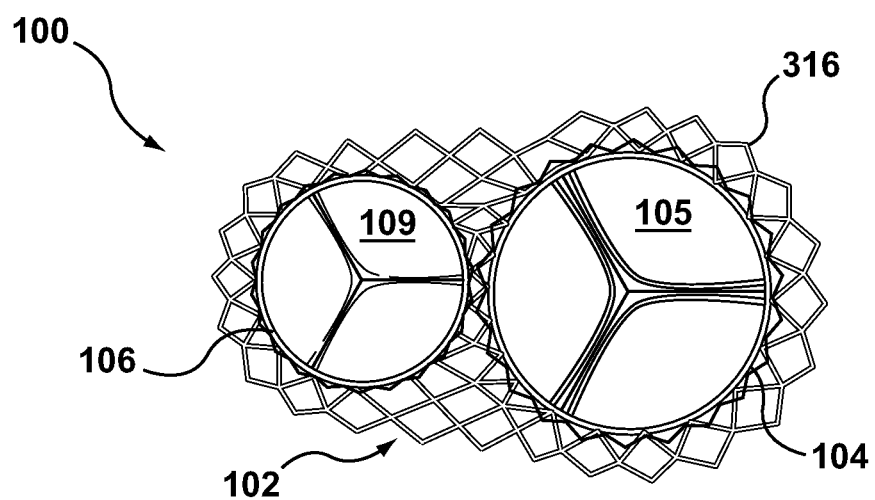
FIG. 2 is a bottom view of the dual valve prosthesis shown in FIG. 1.

Embodiments hereof are related to a dual valve prosthesis configured for deployment within the mitral and aortic valves of the heart in a single transcatheter heart valve implantation procedure. FIG. 1 is a side view of a dual valve prosthesis 100 in an expanded configuration in accordance with an embodiment hereof, with FIG. 2 being a bottom view of dual valve prosthesis 100 as shown expanded in FIG. 1. Dual valve prosthesis 100 includes an anchoring frame 102, a first prosthetic valve assembly 104 and a second prosthetic valve assembly 106. The general direction of blood flow through dual valve prosthesis 100 when deployed in vivo is depicted by arrows BF. Anchoring frame 102 is a self-expanding stent-like framework such that anchoring frame 102 with prosthetic valve assemblies 104, 106 attached thereto may be radially compressed into a delivery configuration within a sheath or other containment structure of a catheter-based delivery system for tracking to a treatment site within the heart and thereafter when released from the sheath will return to the expanded configuration shown in FIG. 1. In an embodiment, anchoring frame 102 may be formed from a mesh made of nitinol wire. The stent-like framework of anchoring frame 102 is shown in embodiments herein to have openings 108 of a diamond shape but openings 108 may be any one of a variety of other shapes without departing from the scope hereof.

Figure 3:
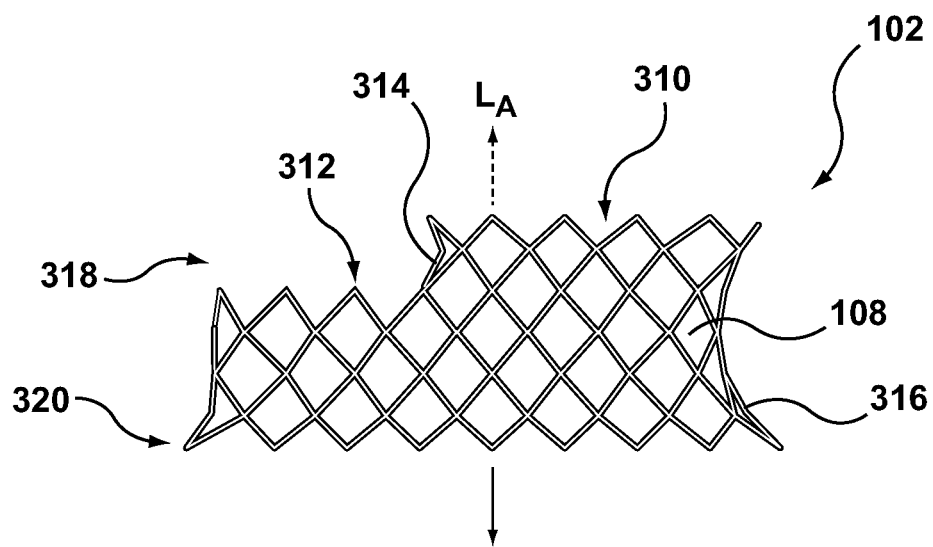
FIG. 3 is a side view of an anchoring frame of the dual valve prosthesis shown in FIG. 1 in an expanded configuration.
Figure 3A:
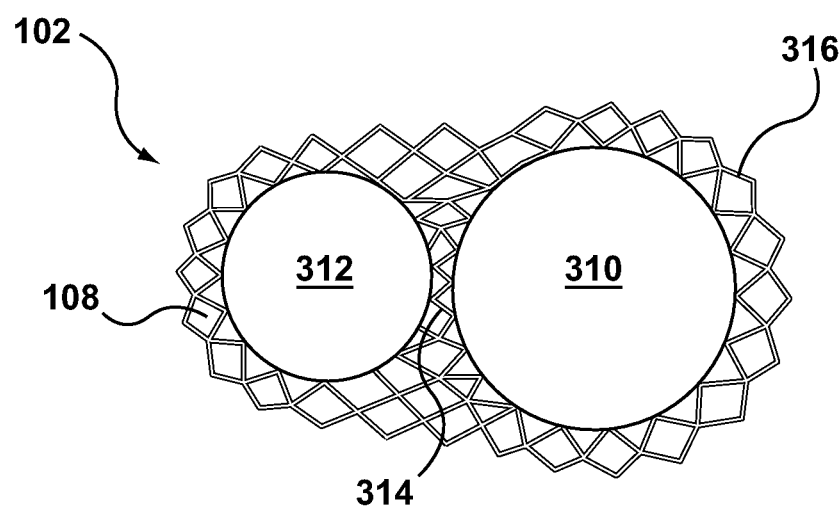
FIG. 3A is a bottom view of the anchoring frame shown in FIG. 3.

FIG. 3 is a side view of anchoring frame 102 in an expanded configuration separated from the remainder of dual valve prosthesis 100 with FIG. 3A being a bottom view of anchoring frame 102 as shown in FIG. 3. The stent-like framework of anchoring frame 102 is formed to define a first or mitral port 310 and a second or aortic port 312 within a first or distal end 318 of anchoring frame 102 and to define an outwardly flaring skirt portion 316 at a second or proximal end 320 of anchoring frame 102. As best shown in the side view of FIG. 3 with reference to longitudinal axis $L_A$, first and second ports 310, 312 are laterally and longitudinally separated or offset from each other by a heel segment 314 of anchoring frame 102 when anchoring frame 102 is in the expanded configuration.

With reference to FIG. 1, each of first and second prosthetic valve assemblies 104, 106 includes a balloon-expandable stent structure 103, 107, respectively, with a prosthetic valve 105, 109, respectively, secured therein. Stent structures 103, 107 are patterned tubular devices that are radially-expandable from a crimped delivery configuration to an expanded deployed configuration by a dilatation balloon. In an embodiment, balloon-expandable stent structures 103, 107 may be formed from stainless steel or other suitable metal, such as platinum iridium, and cobalt chromium alloys such as MP35N. Stent structures 103, 107 may be formed embodiments hereof by a plurality of radially-expandable cylindrical rings, which may be constructed of wire, each having a generally zig-zag pattern, that are connected to each other as would be understood by one of ordinary skill in the art. In other embodiments, stent structures 103, 107 may be formed by laser cutting or etching the lattice-like pattern from a tube or from a flat sheet prior to forming the stent structure. It will be appreciated by one of ordinary skill in the art that the pattern of stent structures 103, 107 of FIG. 1 is merely exemplary and that balloon-expandable stent structures of various forms, patterns and methods of fabrication can be used as would be apparent to one of skill in the art in accordance with various embodiments of the present invention. In other embodiments in accordance herewith, one or both of stent structure 103, 107 of first and second prosthetic valve assemblies 104, 106, respectively, may be made self-expanding like anchoring frame 102.

Prosthetic valves 105, 109 secured within the interior of stent structures 103, 107, respectively, are configured as one-way valves to allow blood flow in one direction and thereby regulate blood flow there through. In the embodiment shown in FIGS. 1 and 2, each of prosthetic valves 105, 109 includes three valve leaflets to form a tricuspid replacement valve, which may be constructed of pericardium material. In another embodiment, one or both of prosthetic valves 105, 109 may be a bicuspid replacement valve or other leaflet structure that closes with pressure on the outflow and opens with pressure on the inflow. In still other embodiments in accordance herewith, one or both of first and second prosthetic valves 105, 109 may be a single leaflet replacement valve or a replacement valve with more than three leaflets. Natural tissue for forming prosthetic valve leaflets for use in prosthetic valve assemblies in accordance with embodiments hereof may be obtained from, for example, heart valves, aortic roots, aortic walls, aortic leaflets, pericardial tissue, such as pericardial patches, bypass grafts, blood vessels, and the like from humans or animals, such as tissue from bovine, equine or porcine origins. Synthetic materials suitable for use as prosthetic valve leaflets in embodiments hereof include DACRON® polyester commercially available from Invista North America S.A.R.L. of Wilmington, Del., polyurethane, GORE-TEX® or other cloth materials, nylon blends, polymeric materials, and vacuum deposition nitinol fabricated materials. One polymeric material from which the replacement valve leaflets can be made is an ultra-high molecular weight polyethylene material commercially available under the trade designation DYNEEMA® from Royal DSM of the Netherlands. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

The valve leaflets of prosthetic valves 105, 109 are sutured or otherwise securely and sealingly attached to the interior surface of stent structures 103, 107, respectively, and/or graft material 111, 113, respectively, that enclose or line stent structures 103, 107 as would be known to one of ordinary skill in the art of prosthetic valve construction. The graft material 111, 113 may be a low-porosity woven fabric, such as polyester, Dacron fabric, or PTFE, which creates a one-way fluid passage when attached to the respective stent structures 103, 107. In one embodiment, the graft material 111, 113 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, the graft material 111, 113 may also be of a natural material such as pericardium or another membranous tissue such as intestinal submucosa.

First and second prosthetic valve assemblies 104, 106 are attached to anchoring frame 102 by sutures or laser welding, if similar materials are used, to be positioned laterally of each other in dual valve prosthesis 100 such that each valve assembly is aligned with one of the respective first and second ports 310, 312 of anchoring frame 102. More particularly, first prosthetic valve assembly 104 is attached to anchoring frame 102 such that stent structure 103 thereof is substantially surrounded by anchoring frame 102 with an inflow end 115 of first prosthetic valve assembly 104 being positioned within first port 310 of anchoring frame 102. In contrast, an inflow end 117 of second prosthetic valve assembly 106 is attached to second port 312 such that stent structure 107 thereof extends away from anchoring frame 102. In an embodiment hereof, when dual valve prosthesis 100 is implanted within the heart having such a construction, the portion of anchoring frame 102 that surrounds first prosthetic valve assembly 104 anchors within the native mitral valve along with stent structure 103 thereof to provide better resistance against displacement or movement of the prosthetic mitral valve during the high pressures that occur during systole. In contrast, only stent structure 107 of second prosthetic valve assembly 106 is needed to anchor the prosthetic aortic valve within the native aortic valve in this embodiment.

As previously noted above with reference to FIG. 1, the general direction of blood flow through dual valve prosthesis 100 when deployed in vivo is depicted by arrows BF. In an embodiment in which dual valve prosthesis 100 is deployed within the heart, as described in more detail below, first prosthetic valve assembly 104 is a replacement mitral valve positioned to replace the native mitral valve and second prosthetic valve assembly 106 is a replacement aortic valve positioned to replace the native aortic valve with anchoring frame 102 expanded to engage at least a "top" or upper area of the left ventricle there around. In an alternate embodiment, first prosthetic valve assembly 104 is a replacement tricuspid valve positioned to replace the native tricuspid valve and second prosthetic valve assembly 106 is a replacement pulmonic valve positioned to replace the native pulmonic valve with anchoring frame 102 expanded to engage at least a "top" or upper area of the right ventricle there around. Anchoring frame 102 so positioned pushes cordae and the native mitral valve leaflets against the wall and septum area of the left ventricle and aids in anchoring dual valve prosthesis 100 during systole and diastole, and more particularly helps to maintain the deployed position of first prosthetic valve assembly 104 within the native mitral valve. In an embodiment, anchoring frame 102 may be covered with a graft material to aid in the prevention of perivalvular leakage around the replacement mitral valve. In addition, anchoring frame 102 acts to make the native mitral valve more cylindrical so that the subsequent expansion of first prosthetic valve assembly 104 is within a more cylindrically-shaped conduit.

Figure 4:
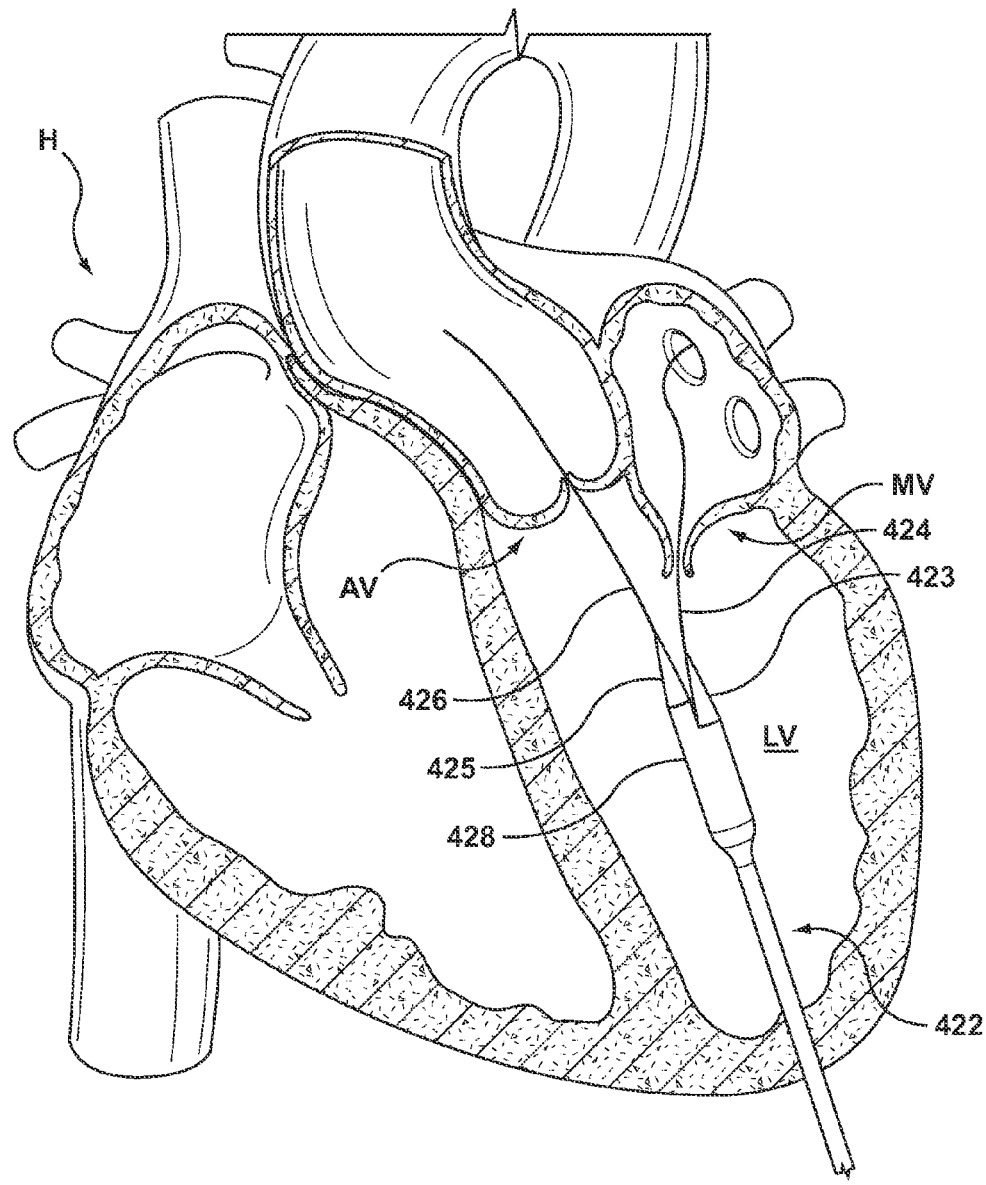
FIGS. 4, 5, 6A, 6B and 7 illustrate a method of deploying the dual valve prosthesis of FIG. 1 within a heart in accordance with an embodiment hereof.

FIGS. 4, 5, 6A, 6B and 7 illustrate a method of performing a concurrent transcatheter valve replacement of the aortic valve and mitral valve of a beating heart in accordance with an embodiment hereof. With reference to FIG. 4, dual valve prosthesis 100 is disposed in a delivery configuration within a distal portion of a delivery catheter 422 that is positioned within a left ventricle LV of a heart H. In the delivery configuration, first prosthetic valve assembly 104 is crimped or otherwise mounted onto a balloon of a first balloon catheter 423 of delivery catheter 422, second prosthetic valve assembly 106 is crimped or otherwise mounted onto a balloon of a second balloon catheter 425 of delivery catheter 422, and anchoring frame 102 is held in a compressed state within a sheath component 428 of delivery catheter 422.

Delivery catheter 422 is shown in FIGS. 4, 5, 6A and 6B having been introduced into the left ventricle LV via a transapical minimally invasive procedure. Delivery catheter 422 so positioned has been tracked through purse-string sutures (not shown) previously placed in the left ventricular apex that are tightened around the delivery catheter or through a hemostasis delivery port/valve to minimize blood leakage from the heart H during the replacement valve implantation procedure, as would be understood by one of ordinary skill in the art. A first guidewire 424 is positioned to extend through mitral valve MV and first balloon catheter 423 with proximal ends (not shown) of first guidewire 424 and first balloon catheter 423 being accessible to a clinician at a proximal end (not shown) of delivery catheter 422. Similarly, a second guidewire 426 is positioned to extend through aortic valve AV and corresponding second balloon catheter 425 with proximal ends (not shown) of second guidewire 426 and second balloon catheter 425 being accessible to the clinician at the proximal end of delivery catheter 422. With reference to FIG. 4, delivery catheter 422 is distally advanced until the "V" of the catheter wedges across the anterior leaflet of the native mitral valve between the aortic and mitral valve annulus.

Figure 5:
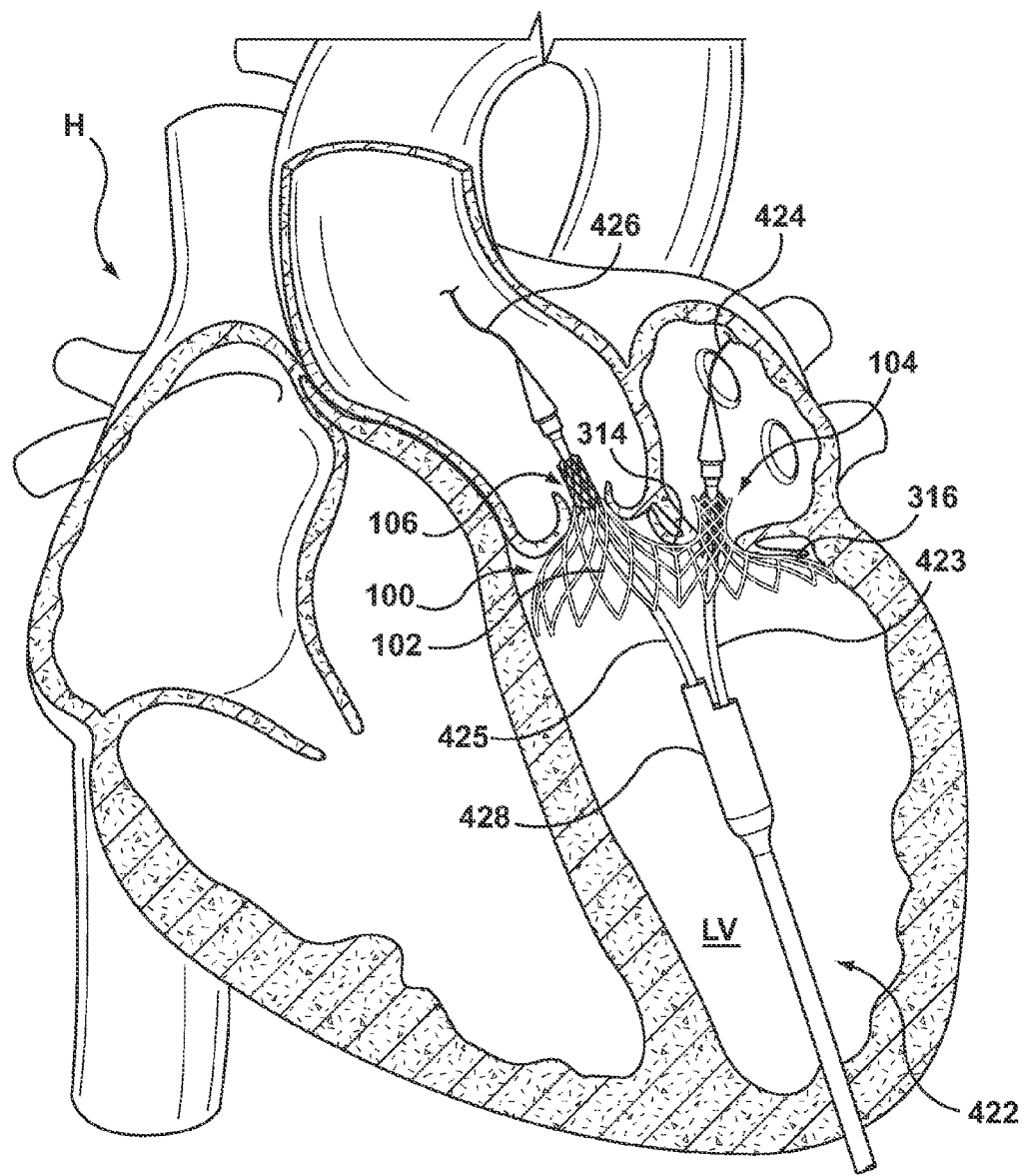

First balloon catheter 423 and second balloon catheter 425 are distally advanced from delivery catheter 422 over respective first and second guidewires 424, 426 to position first prosthetic heart valve assembly 104 within the native mitral valve MV and to position second prosthetic heart valve assembly 106 within the native aortic valve AV. As best shown in FIG. 5, first and second balloon catheters 423, 425 are advanced while delivery catheter 422 is retracted. This action frees or otherwise releases anchoring frame 102 from sheath component 428 so that anchoring frame 102 is permitted to self-expand into contact with an area at the top of the left ventricle LV that surrounds the native mitral and aortic valves. In an embodiment, deployment of anchoring frame 102 is controlled by the clinician to occur when the heart is in diastole such that heel segment 314 of anchoring frame 102 captures and pushes the anterior leaflet of the native mitral valve toward and/or against the continuous aortic mitral fibrous membrane while the skirt portion 316 of anchoring frame 102 captures and pushes the posterior leaflet of the native mitral valve and cordae toward and/or against the ventricle wall.

Figure 6A:
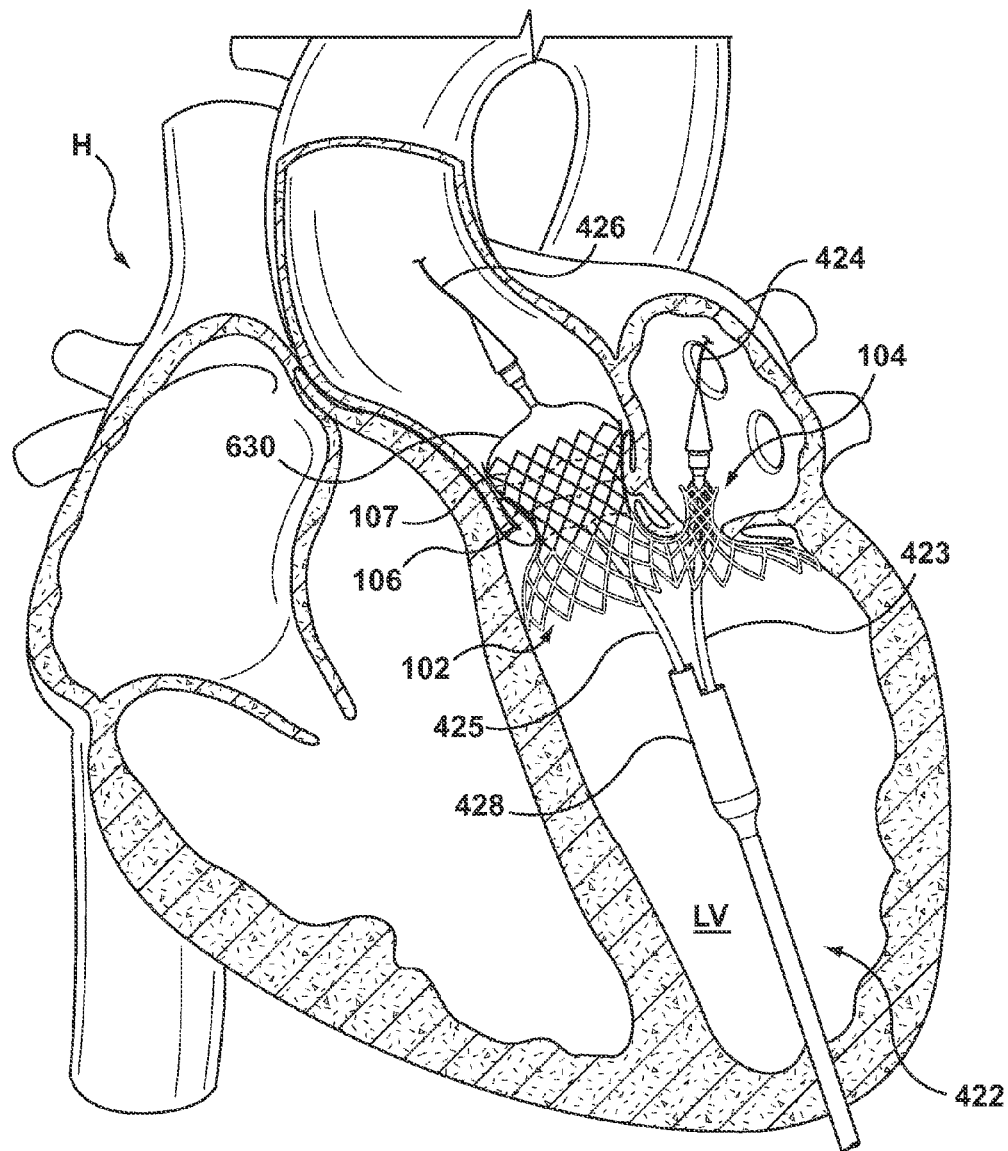
Figure 6B:
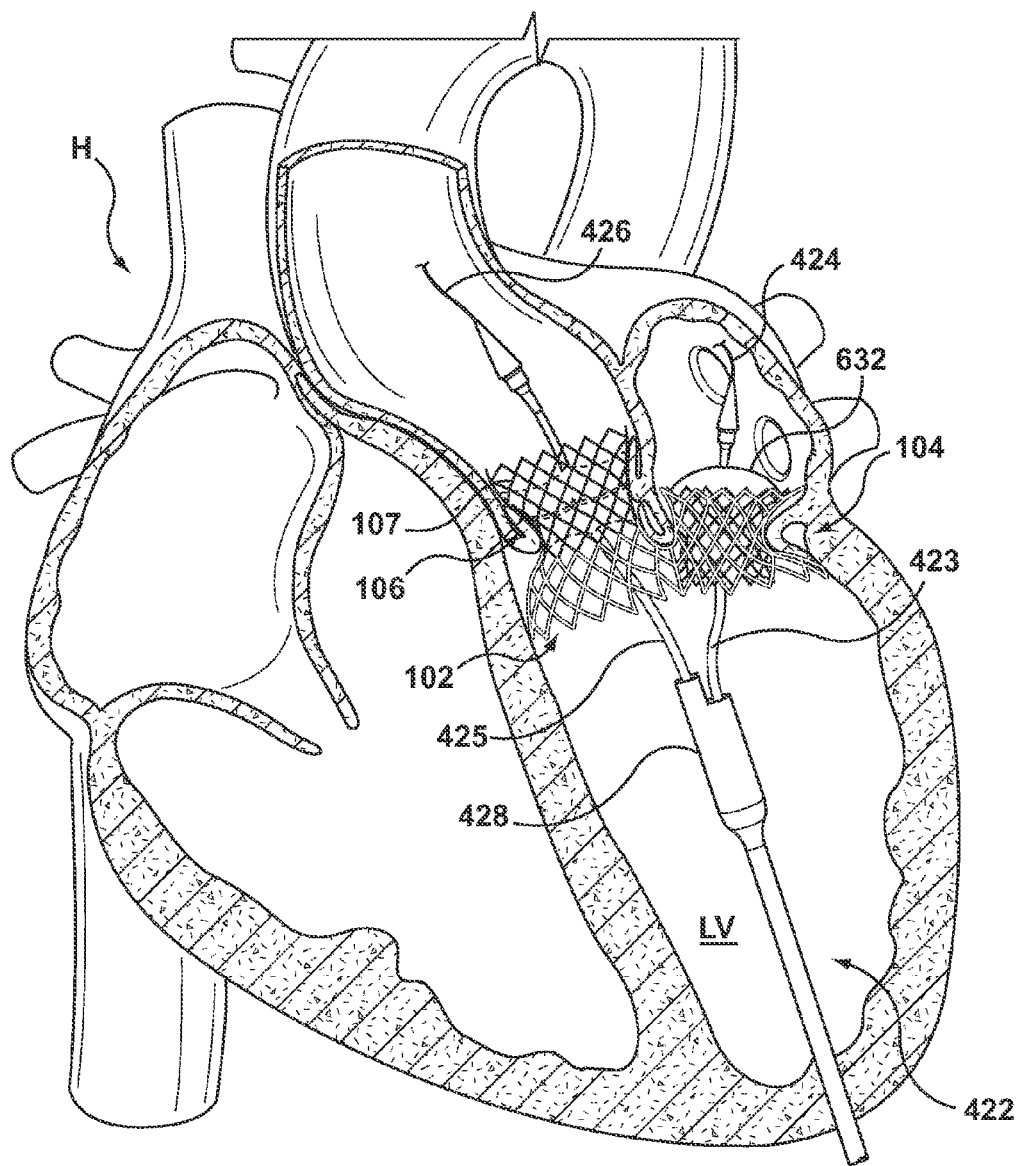

Second prosthetic valve assembly 106 is deployed or implanted within the native aortic valve AV by expanding dilatation balloon 630 of second balloon catheter 425, as shown in FIG. 6A. In an embodiment, deploying second prosthetic heart valve assembly 106 within the heart H includes expanding stent structure 107 thereof into contact with the native aortic valve to anchor the valve assembly therein. Similar to deployment of the second prosthetic valve assembly, first prosthetic valve assembly 104 is deployed or implanted within the native mitral valve MV by expanding dilatation balloon 632 of first balloon catheter 423, as shown in FIG. 6B. In an embodiment, deploying first prosthetic heart valve assembly 104 includes expanding stent structure 103 thereof into contact with a portion of anchoring frame 102 that surrounds first prosthetic valve assembly 104, wherein the anchoring frame portion has been previously positioned to extend between the left ventricle LV and the left atria LA through the native mitral valve to aid in anchoring first prosthetic valve assembly 104 therein. In accordance with another embodiment hereof, second prosthetic valve assembly 106 may be deployed within the native aortic valve prior to the deployment of first prosthetic valve assembly 104 being deployed within the native mitral valve in order to act in conjunction with anchoring frame 102 as an anchor to dual valve prosthesis 100 and thereby aid in the proper positioning of first prosthetic valve assembly 104 within the native mitral valve prior to its deployment/implantation therein. After implantation of dual valve prosthesis 100, each of dilatation balloons 630, 632 is deflated and the first and second balloon catheters 423,425 along with the remainder of delivery catheter 422 are removed from the heart with the purse-string sutures noted above being tightened thereafter to close the opening in the left ventricular apex.

Figure 7:
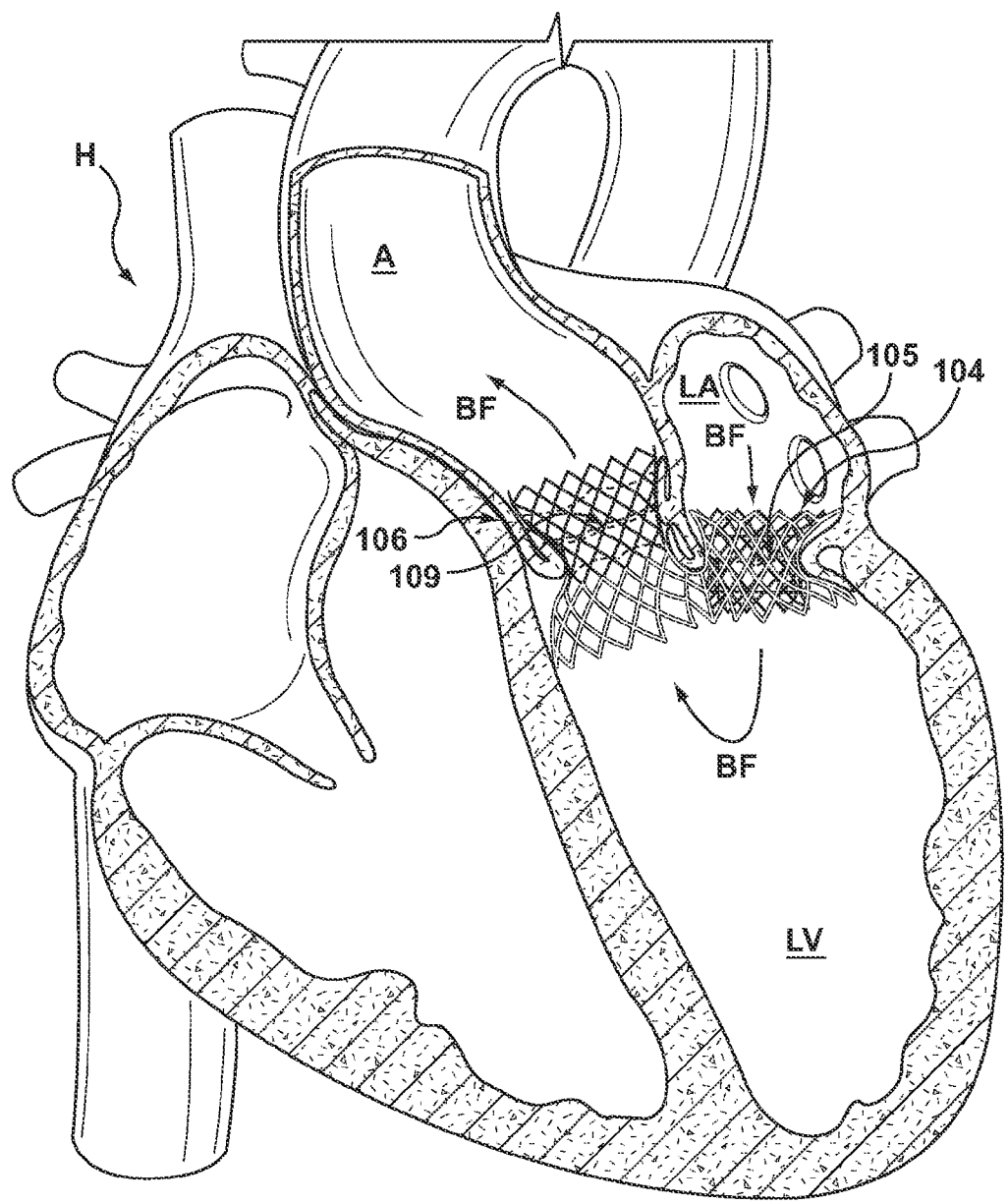

FIG. 7 depicts dual valve prosthesis 100 implanted within the heart H with first prosthetic valve assembly 104 implanted to replace the native mitral valve and second prosthetic valve assembly 106 implanted to replace the native aortic valve. With a comparison of FIG. 1 and FIG. 7, prosthetic mitral valve 105 is a one-way valve that is configured to be positioned in the heart between the left atrium LA and left ventricle LV to permit blood flow through inflow end 115 of first prosthetic valve assembly 104 in the direction of arrows BF during atrial emptying and ventricular filling when the leaflets of prosthetic mitral valve 105 are configured to open or part toward the left ventricle LV. Prosthetic aortic valve 109 is a one-way valve that is configured to be positioned in the heart between the left ventricle LV and the aorta A to permit blood flow through inflow end 117 of second prosthetic valve assembly 106 in the direction of arrows BF during systole when the leaflets of prosthetic aortic valve 109 are configured to open or part toward the aorta A. In embodiments hereof, each of prosthetic mitral valve 105 and prosthetic aortic valve 107 may be a bioprosthetic trileaflet heart valve such as any one of the bioprosthetic heart valves being used in implantable heart valve devices currently available that has been adapted for use herein.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A dual valve prosthesis for concurrent deployment within first and second adjacent native valves comprising:
   an anchoring frame having an expandable framework;
   a first prosthetic valve assembly configured for deployment within the first native valve, the first prosthetic valve assembly being attached to the anchoring frame; and
   a second prosthetic valve assembly configured for concurrent deployment within the adjacent second native valve, the second prosthetic valve assembly being attached to the anchoring frame to be laterally separated from the first prosthetic valve assembly by a portion of the anchoring frame, wherein the portion of the anchoring frame is configured to extend between the first and second adjacent native valves when the dual valve prosthesis is deployed, and
   wherein each of the first and second prosthetic valve assemblies includes a balloon-expandable stent structure with a prosthetic valve secured therein.

2. The dual valve prosthesis of claim 1, wherein the expandable framework of the anchoring frame is self-expanding.

3. The dual valve prosthesis of claim 2, wherein the expandable framework of the anchoring frame is formed from a mesh made of nitinol wire.

4. The dual valve prosthesis of claim 2, wherein each of the stent structures of the first and second prosthetic valve assemblies is attached to the anchoring frame by sutures.

5. The dual valve prosthesis of claim 1, wherein the anchoring frame includes first and second ports, wherein the first prosthetic valve assembly is attached to the anchoring frame such that the balloon-expandable stent structure of the first prosthetic valve assembly is substantially surrounded by the anchoring frame with an inflow end of the first prosthetic valve assembly being positioned proximate the first port.

6. The dual valve prosthesis of claim 5, wherein an inflow end of the second prosthetic valve assembly is attached to the second port such that the balloon-expandable stent structure of the second prosthetic valve assembly extends from the anchoring frame.

7. The dual valve prosthesis of claim 6, wherein the anchoring frame includes a skirt portion that flares outwardly when the anchoring frame is in an expanded configuration.

8. The dual valve prosthesis of claim 1, wherein the anchoring frame is at least partially covered by a graft material.

9. The dual valve prosthesis of claim 1, wherein the prosthetic valve of the first prosthetic valve assembly is a prosthetic mitral valve.

10. The dual valve prosthesis of claim 9, wherein the prosthetic valve of the second prosthetic valve assembly is a prosthetic aortic valve.

11. A dual valve prosthesis for concurrent deployment within a mitral valve and an aortic valve comprising:
   an anchoring frame;
   a prosthetic mitral valve assembly having a balloon-expandable stent structure attached to the anchoring frame and having a prosthetic mitral valve secured the balloon-expandable stent structure, wherein the balloon-expandable stent structure of the prosthetic mitral valve assembly extends within and is surrounded by the anchoring frame; and a prosthetic aortic valve assembly having a balloon-expandable stent structure attached to the anchoring frame to be laterally offset from the balloon-expandable stent structure of the prosthetic mitral valve assembly and having a prosthetic aortic valve secured therein, wherein the balloon-expandable stent structure of the prosthetic aortic valve assembly is attached to the anchoring frame such that the balloon-expandable stent structure of the prosthetic aortic valve assembly extends away from the anchoring frame, wherein a portion of the prosthetic aortic valve assembly extends within and is surrounded by the anchoring frame.

12. The dual valve prosthesis of claim 11, wherein the anchoring frame has a self-expanding framework.

13. The dual valve prosthesis of claim 12, wherein the self-expanding framework of the anchoring frame is formed from a mesh made of nitinol wire.

14. The dual valve prosthesis of claim 11, wherein the anchoring frame includes a mitral port and an aortic port at a first end thereof with an inflow end of the balloon-expandable stent structure of the prosthetic mitral valve assembly being attached to the mitral port to extend within the anchoring frame therefrom and with an inflow end of the balloon-expandable stent structure of the prosthetic aortic valve assembly being attached to the aortic port to extend away from the anchoring frame therefrom.

15. The dual valve prosthesis of claim 14, wherein the anchoring frame includes a skirt portion at an opposing second end thereof that flares outwardly when the anchoring frame is in an expanded configuration.

16. A dual valve prosthesis for deployment within first and second adjacent native valves comprising:

an anchoring frame defining laterally separated first and second ports at a first end thereof and a skirt portion at a second end thereof, wherein the skirt portion flares outwardly when the anchoring frame is in an expanded configuration;

a first prosthetic valve assembly configured for deployment within the first native valve, the first prosthetic valve assembly having a stent structure with an inflow end attached to the anchoring frame at the first port and having a first prosthetic valve secured therein; and a second prosthetic valve assembly configured for deployment within the adjacent second native valve, the second prosthetic valve assembly having a stent structure with an inflow end attached to the anchoring frame at the second port and having a second prosthetic valve secured therein, wherein respective stent structures of the first and second prosthetic valve assemblies are disposed on the anchoring frame to be laterally separated from each other by a portion of the anchoring frame.

17. The dual valve prosthesis of claim 16, wherein the first prosthetic valve assembly extends within the anchoring frame from the first port to be substantially surrounded by the anchoring frame.

18. The dual valve prosthesis of claim 17, wherein the second prosthetic valve assembly extends away from the anchoring frame from the second port.

19. The dual valve prosthesis of claim 16, wherein the first and second ports of the anchoring frame are longitudinally offset from each other.

20. The dual valve prosthesis of claim 16, wherein the stent structures of each of the first and second prosthetic valve assemblies is balloon-expandable with the respective first and second prosthetic valves being secured therein.

\* \* \* \* \*